US012605071B2

(12) United States Patent      (10) Patent No.:   US 12,605,071 B2

Wu et al.          (45) Date of Patent:     Apr. 21, 2026

(54) COMPATIBLE SYSTEM AND METHOD FOR SYNCHRONIZED WORKING OF MAGNETIC RESONANCE IMAGING AND FOCUSED ULTRASOUND THERMAL ABLATION

(71) Applicants: Shanghai Shende Green Medical Era Healthcare Technology Co., Ltd., Shanghai (CN); Shende (Ningbo) Medical Device Technology Co., Ltd, Ningbo (CN); Nantong Shende Medical Device Technology Co., Ltd, Nantong (CN)

(72) Inventors: Hao Wu, Shanghai (CN); Shenyan Zong, Shanghai (CN); Shu Liu, Shanghai (CN); Jiabao Wen, Shanghai (CN)

(73) Assignees: Shanghai Shende Green Medical Era Healthcare Technology Co., Ltd., Shanghai (CN); Shende (Ningbo) Medical Device Technology Co., Ltd, Ningbo (CN); Nantong Shende Medical Device Technology Co., Ltd, Nantong (CN)

( * ) Notice: Subject to any disclaimer, the term of this patent is extended or adjusted under 35 U.S.C. 154(b) by 0 days.

(21) Appl. No.: 18/659,313

(22) Filed: May 9, 2024

(65) Prior Publication Data

US 2024/0285166 A1     Aug. 29, 2024

Related U.S. Application Data

(63) Continuation of application No. PCT/CN2022/130565, filed on Nov. 8, 2022.

(30) Foreign Application Priority Data

Nov. 9, 2021    (CN) ......................... 202111317148.4

(51) Int. Cl.
    *A61B 5/00*         (2006.01)
    *A61B 5/055*        (2006.01)
         (Continued)

(52) U.S. Cl.
    CPC ............ *A61B 5/0036* (2018.08); *A61B 5/055* (2013.01); *A61B 17/320068* (2013.01);
         (Continued)

(58) Field of Classification Search
    CPC .. A61B 17/320068; A61B 2017/00039; A61B 2017/320069; A61B 2090/374;
         (Continued)

(56) References Cited

U.S. PATENT DOCUMENTS

| | | |
|---|---|---|
| 10,571,540 B2 | 2/2020 | Assif |
| 2001/0049474 A1 | 12/2001 | Wagshul |

(Continued)

FOREIGN PATENT DOCUMENTS

| | | |
|---|---|---|
| CN | 1957263 A | 5/2007 |
| CN | 101904746 A | 12/2010 |

(Continued)

OTHER PUBLICATIONS

First Office Action issued in counterpart Russian Patent Application No. 2024115293, dated Dec. 6, 2024.

(Continued)

*Primary Examiner* — Michael J Carey
*Assistant Examiner* — Maria Christina Talty
(74) *Attorney, Agent, or Firm* — Westbridge IP LLC

(57) ABSTRACT

Disclosed are a compatible system and a compatible method for synchronize working of magnetic resonance imaging and focused ultrasound thermal ablation. The compatible system for synchronize working includes a magnetic resonance device and a focused ultrasound device, further includes a signal collector and a control circuit connected to the signal (Continued)

301 → recording trigger time of RF signal ← deleting the record and waiting for the next RF signal → 304

↓ calculating time difference of trigger signal

↓

302 → comparing the time difference and TR cycle → error > 0.5 ms

↓ error ≤ 0.5 ms

303 → generating trigger to make the focused ultrasound device to work collector. In an imaging process of the magnetic resonance device, the signal collector is configured to detect a radio frequency (RF) signal of the magnetic resonance device, and the control circuit is configured for recording a trigger time of the RF signal, generating an enable signal triggering the focused ultrasound device to start heating based on the trigger time of the RF signal, and controlling a heating duration of the focused ultrasound device according to an echo time.

8 Claims, 2 Drawing Sheets

(51) Int. Cl.

| | | |
|---|---|---|
| *A61B 17/32* | (2006.01) | |
| *G01R 33/54* | (2006.01) | |
| *G16H 40/63* | (2018.01) | |
| *A61B 17/00* | (2006.01) | |

(52) U.S. Cl.
CPC .......... *G01R 33/543* (2013.01); *G16H 40/63* (2018.01); *A61B 2017/00039* (2013.01); *A61B 2017/320069* (2017.08)

(58) Field of Classification Search
CPC ........ A61B 5/0036; A61B 5/055; A61N 7/02; G01R 33/4804; G01R 33/4814; G01R 33/543; G16H 20/40; G16H 40/20; G16H 40/63
See application file for complete search history.

(56) References Cited

U.S. PATENT DOCUMENTS

| | | | | |
|---|---|---|---|---|
| 2002/0193681 | A1* | 12/2002 | Vitek | ...................... G01R 33/28 |
| | | | | 600/411 |
| 2015/0190659 | A1* | 7/2015 | Kohler | .................... A61B 5/015 |
| | | | | 600/411 |
| 2016/0139224 | A1* | 5/2016 | Assif | .................... A61B 8/4416 |
| | | | | 600/411 |
| 2016/0331262 | A1* | 11/2016 | Kuck | ...................... A61N 7/022 |
| 2017/0281042 | A1 | 10/2017 | Miller et al. | |

FOREIGN PATENT DOCUMENTS

| | | | |
|---|---|---|---|
| CN | 102019044 | A | 4/2011 |
| CN | 102247163 | A | 11/2011 |
| CN | 104602761 | A | 5/2015 |
| CN | 107205718 | A | 9/2017 |
| CN | 107405502 | A | 11/2017 |
| CN | 109939368 | A | 6/2019 |
| CN | 114145732 | A | 3/2022 |
| DE | 60233402 | | 10/2009 |
| WO | 2020037237 | A1 | 2/2020 |
| WO | 2021116763 | A1 | 6/2021 |

OTHER PUBLICATIONS

Second Office Action issued in counterpart Chinese Patent Application No. 202111317148.4, dated Dec. 30, 2024.
First Office Action issued in counterpart Chinese Patent Application No. 202111317148.4, dated Jun. 7, 2024.
International Search Report and Written Opinion issued in corresponding PCT Application No. PCT/CN2022/130565, dated Jan. 19, 2023.

* cited by examiner

301 — recording trigger time of RF signal

304 — deleting the record and waiting for the next RF signal calculating time difference of trigger signal 302 — comparing the time difference and TR cycle error > 0.5 ms error ≤ 0.5 ms 303 — generating trigger to make the focused ultrasound device to work

COMPATIBLE SYSTEM AND METHOD FOR SYNCHRONIZED WORKING OF MAGNETIC RESONANCE IMAGING AND FOCUSED ULTRASOUND THERMAL ABLATION

CROSS-REFERENCE TO RELATED APPLICATIONS

The present application is a continuation application of International Application No. PCT/CN2022/130565, filed on Nov. 8, 2022, which claims priority to Chinese Patent Application No. 202111317148.4, filed on Nov. 9, 2021. The disclosures of the above-mentioned applications are incorporated herein by reference in their entireties.

TECHNICAL FIELD

The present application relates to intelligent medical devices, and in particular to a compatible system for synchronize working of magnetic resonance imaging and focused ultrasound thermal ablation, and a compatible method for synchronize working of magnetic resonance imaging and focused ultrasound thermal ablation.

BACKGROUND

Focused ultrasound thermal ablation treatment utilizes ultrasound to focus on the target area together. The energy of the ultrasound can generate a high temperature of more than 65° C. in the target area to kill the tissue to achieve the purpose of treatment. At the same time, magnetic resonance imaging scans the treated area and can obtain phase changes caused by temperature to monitor the treatment process in real time, and the feedback temperature changes can ensure the effectiveness and safety of the treatment. Currently, magnetic resonance guided focused ultrasound thermal ablation technology, as a non-invasive and effective treatment method, has been used in the clinical treatment of uterine fibroids, essential tremor and other diseases.

Focused ultrasound thermal ablation utilizes the biological thermal effect of ultrasound. The combined action of multiple ultrasound beams will cause the tissue to reach a sufficiently high temperature. Generally speaking, when the cell temperature is higher than 40° C., the cells stop growing, and when the cell temperature reaches 45° C., the protein begins to denature. If the temperature continues to rise, the protein will decompose, that is, the cells will be killed. The temperature measurement of the magnetic resonance is based on the change in the proton resonance frequency in the tissue caused by temperature changes. In the experiment, it was measured that at a magnetic field strength of 3 T, the rate of change of the proton resonance frequency with temperature is 1.28 Hz/° C. The change in proton resonance frequency is mapped to the magnetic resonance image as a phase change in the focal area of the image. Usually, a gradient echo sequence is performed on the magnetic resonance to scan the target layer, and the phase change map of the treatment area during the thermal ablation process, that is, the temperature change during the treatment process, can be obtained in real time.

However, when working simultaneously with the magnetic resonance scanning and the focused ultrasound thermal ablation treatment, mutual interference between the magnetic resonance and the focused ultrasound thermal ablation is inevitable. Especially when the focused ultrasound is working, there is a certain amount of electromagnetic leakage in the transducer, and the leaked signal will be coupled into the signal acquisition of the magnetic resonance, and ultimately reducing the image signal-to-noise ratio. The accuracy of temperature measurement of the magnetic resonance is directly proportional to the signal-to-noise ratio of the image. Therefore, how to implement the synchronize working without interference between the magnetic resonance and the focused ultrasound thermal ablation is an urgent technical issue in this field that needs to be solved.

SUMMARY

The purpose of the present application is to provide a compatible system for synchronize working of magnetic resonance imaging and focused ultrasound thermal ablation and a compatible method for synchronize working of magnetic resonance imaging and focused ultrasound thermal ablation with good compatibility and high safety, so as to overcome the shortcomings of the above-mentioned prior art.

The object of the present application can be achieved by the following technical solutions.

A compatible system for synchronize working of magnetic resonance imaging and focused ultrasound thermal ablation, including a magnetic resonance device and a focused ultrasound device, the magnetic resonance device and the focused ultrasound device can be any of magnetic resonance devices and focused ultrasound devices existing in the prior art; and the system further includes a signal collector and a control circuit connected to the signal collector; and in an imaging process of the magnetic resonance device, the signal collector is configured to detect a radio frequency (RF) signal of the magnetic resonance device, and the control circuit is configured for recording a trigger time of the RF signal, generating an enable signal triggering the focused ultrasound device to start heating based on the trigger time of the RF signal, and controlling a heating duration of the focused ultrasound device according to an echo time TE.

Furthermore, the generating the enable signal triggering the focused ultrasound device to start working based on the trigger time of the RF signal is specifically:

calculating an error value between a trigger time difference and a time of repetition (TR) cycle according to the trigger time difference between a current trigger time of the RF signal and an adjacent last trigger time of the RF signal, and determining whether the error value is less than a set threshold value: in response to the error value being less than the set threshold value, generating the enable signal at the current trigger time of the RF signal; and in response to the error value being not less than the set threshold value, deleting the current trigger time of the RF signal.

Furthermore, the set threshold value is less than 1 ms.

Furthermore, the control circuit is configured to obtain the trigger time of the RF signal by comparing voltage values of the RF signal, and record the trigger time.

Furthermore, the heating duration of the focused ultrasound device is controlled to be less than the echo time TE.

Furthermore, the signal collector is an open-loop coil.

Furthermore, a heating of the focused ultrasound device is less than or equal to a phase encoding number of imaging of the magnetic resonance device.

The present application further provides a compatible method for synchronize working of magnetic resonance imaging and focused ultrasound thermal ablation, the method is configured for controlling a magnetic resonance device and a focused ultrasound device to work alternately and compatibly, and the method includes:

in an imaging process of the magnetic resonance device, detecting a RF signal of the magnetic resonance device, recording a trigger time of the RF signal, generating an enable signal triggering the focused ultrasound device to start heating based on the trigger time of the RF signal, and controlling a heating duration of the focused ultrasound device according to an echo time TE.

Furthermore, the generating the enable signal triggering the focused ultrasound device to start working based on the trigger time of the RF signal is specifically:

calculating an error value between a trigger time difference and a time of repetition (TR) cycle according to the trigger time difference between a current trigger time of the RF signal and an adjacent last trigger time of the RF signal, and determining whether the error value is less than a set threshold value: in response to the error value being less than the set threshold value, generating the enable signal at the current trigger time of the RF signal; and in response to the error value being not less than the set threshold value, deleting the current trigger time of the RF signal.

Furthermore, the heating duration of the focused ultrasound device is controlled to be less than the echo time TE.

Compared with the prior art, the present application has the following beneficial effects.

Firstly, the present application rationally utilizes the acquisition time of non-signals in magnetic resonance imaging and controls the heating work of the focused ultrasound device, so that the two can achieve synchronized work.

Secondly, during the time period of magnetic resonance signal collection, the focused ultrasound device stops working, which avoids mutual electromagnetic interference between the two, and achieves perfect compatibility between the two.

Lastly, the present application detects and corrects the accuracy of the trigger time of the RF signal, thereby improving control reliability.

DETAILED DESCRIPTION OF THE EMBODIMENTS

The present application will be described in detail below with reference to the accompanying drawings and specific embodiments. The embodiment is implemented based on the technical solution of the present application and provides detailed implementation modes and specific operating procedures. However, the scope of the present application is not limited to the following embodiments.

Theoretically, the two important known parameters of gradient echo sequence in imaging respectively are time of repetition TR and echo time TE. TR represents the time interval of phase encoding, that is, the time interval between each radio frequency pulse (RF) excitation, and this time interval is called a TR cycle (time of repetition cycle). After each RF excitation, the effect of the gradient can form an echo within the current TR cycle, and the time from the RF pulse center to the echo center is TE. Usually, magnetic resonance only collects signals within a range of ±1 ms from the center of the echo. In a gradient echo sequence suitable for temperature measurement, a TR cycle is usually 15 ms~20 ms. The inventor found by comparison that the signal acquisition time of magnetic resonance is shorter than a TR cycle. That is, within a TR cycle, part of the "dead time" that is not related to imaging can be configured for a focused ultrasound treatment work.

Figure 1:
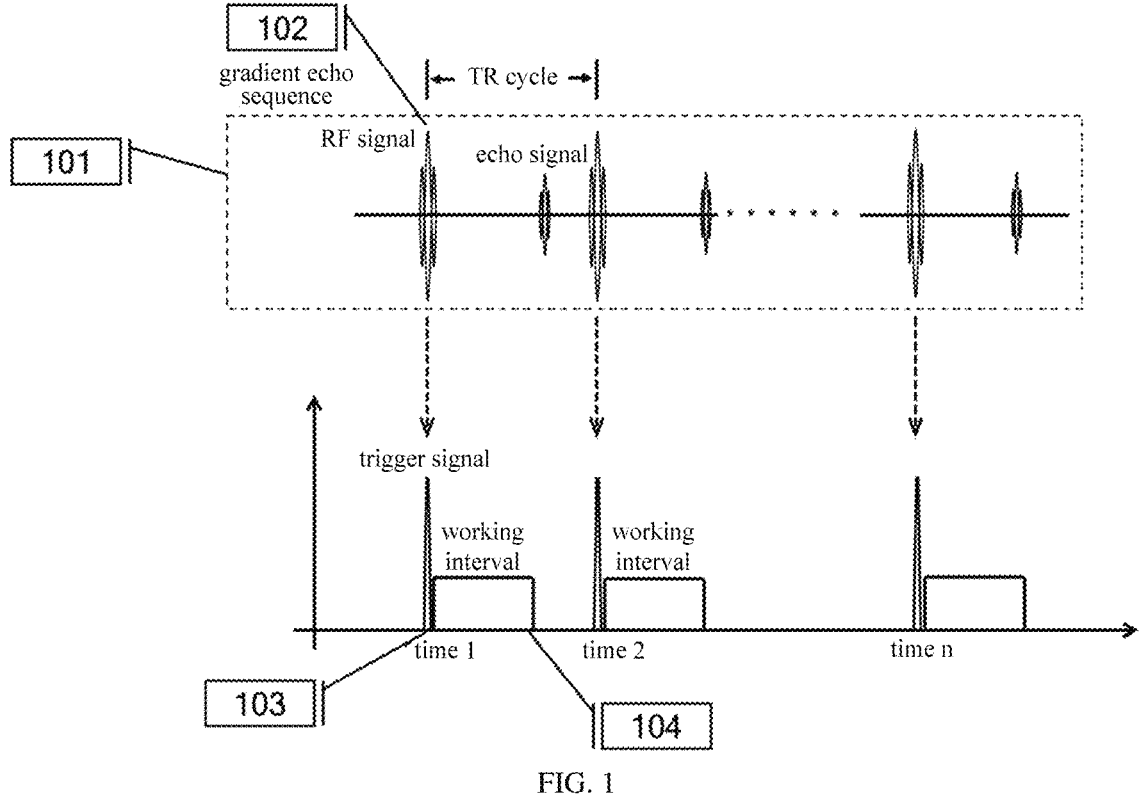
FIG. 1 is a schematic view of basic principles of the present application.

The present application uses the "dead time" within the TR cycle to control the focused ultrasound device to achieve synchronization between the two without interfering with each other. As shown in FIG. 1, the principle of the present application is: the magnetic resonance device scans the target layer by the gradient echo sequence 101, detects a RF signal 102 of each gradient echo sequence 101, records the time of the center of each RF pulse as the trigger time of the RF signal, generates an enable signal triggering the focused ultrasound device to start heating based on the trigger time of the RF signal, the time of enable signal is 103, and controls a heating duration of the focused ultrasound device according to echo time TE. The heating stop time of the focused ultrasound device is 104. By controlling the working time sequence of the focused ultrasound device, the heating process works within the time period of non-magnetic resonance signal acquisition. Finally, the above process is repeated continuously in the magnetic resonance imaging process to complete the work of synchronization and compatibility between the two.

Figure 3:
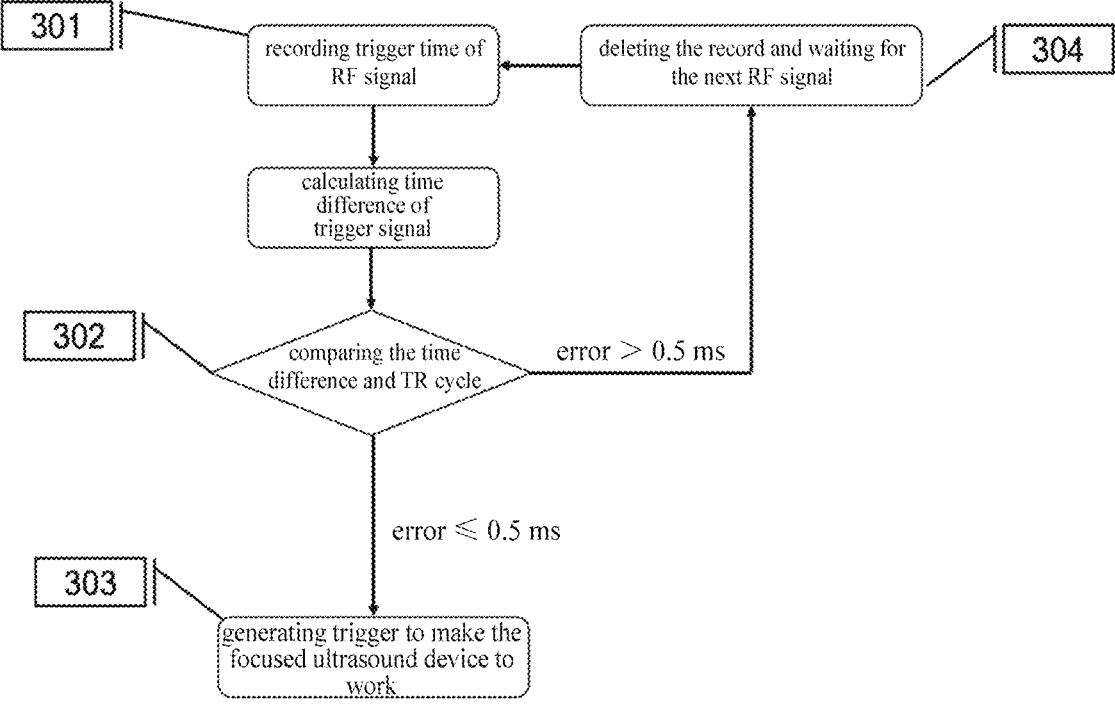
FIG. 3 is an error correction control flow chart according to steps of the present application.

In order to further improve the accuracy, the present application further performs error correction and confirmation on the trigger time of the RF signal. As shown in FIG. 3, the specific steps to generate the enable signal triggering the focused ultrasound device to start working based on the trigger time of the RF signal include the follows.

301. Obtaining the trigger time of the RF signal by comparing the voltage value of the RF signal, recording, and calculating the trigger time difference between the current trigger time of the RF signal and the adjacent last trigger time of the RF signal.

302. Calculating an error value between the trigger time difference and a TR cycle, and determining whether the error value is less than a set threshold value. The set threshold value is less than 1 ms. If the error value is less than the set threshold value, the trigger is considered correct and step 303 is executed. If the error value is not less than the set threshold value, the RF signal is considered incorrect and step 304 is executed.

303. Generating the enable signal at the current trigger time of the RF signal. The enable signal is an extremely short pulse to cause the focused ultrasonic device to start to work.

304. Deleting the current trigger time of the RF signal, do not generate an enable signal, and waiting for the next RF signal.

By the above-mentioned method of alternating work, realizing the synchronous working and full compatibility of the magnetic resonance scanning and the focused ultrasound device, thus improving the working safety and accuracy of magnetic resonance device and focused ultrasound device.

First Embodiment

Figure 2:
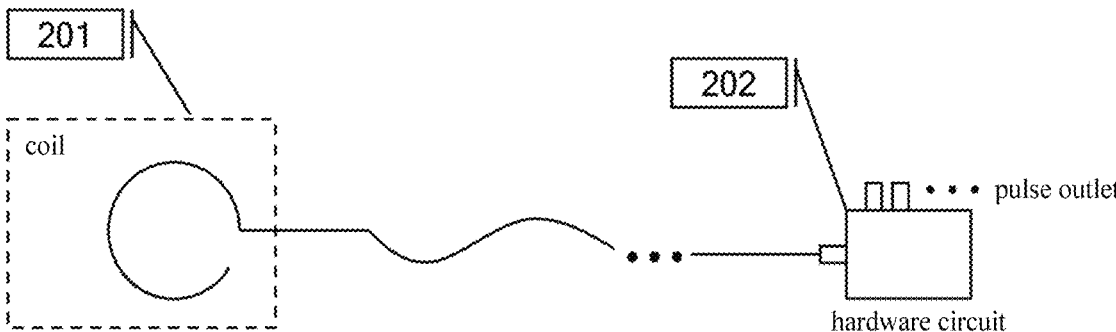
FIG. 2 is a partial structural schematic view of a system of the present application.

This embodiment provides a compatible system for the synchronize working of the magnetic resonance imaging and the focused ultrasound thermal ablation, including a magnetic resonance device, a focused ultrasound device, a signal collector 201, and a control circuit 202. As shown in FIG. 2, in an imaging process of the magnetic resonance device, the signal collector 201 detects a RF signal of the magnetic resonance device, and the control circuit 202 records a trigger time of the RF signal, generates an enable signal triggering the focused ultrasound device to start heating based on the trigger time of the RF signal, and controls a heating duration of the focused ultrasound device according to echo time TE.

In this embodiment, the signal collector 201 uses a simple open-loop coil to detect the RF signal of magnetic resonance. The control circuit 202 has the function of comparing the RF signal voltage, recording and judging the relationship between the RF cycle and the known TR cycle, and generating a trigger signal to make the focused ultrasound device work.

The synchronization control working process of the above compatible system includes:

a. detecting the RF signal of magnetic resonance by a simple open-loop coil;

b. comparing and correcting the voltage peak of the RF signal by the hardware control circuit, forming a trigger signal controlling the working of the focused ultrasound device, and recording the time;

c. combined with the known echo time TE, controlling the heating of the focused ultrasound device in the "dead time", and waiting for the next trigger after the heating is completed; and d. during the process of magnetic resonance imaging, repeating step a to step c until a single magnetic resonance image acquisition is completed. The number of times of repetitions of step a to step c is equal to a phase encoding number of imaging, which usually is 128 times.

In this embodiment, the set threshold value in the error correction mechanism is set to 0.5 ms.

Second Embodiment

This embodiment provides a compatible method for the synchronize working of the magnetic resonance imaging and the focused ultrasound thermal ablation. The method is configured for controlling the alternate and compatible work of a magnetic resonance device and a focused ultrasound device, and includes the following steps: in an imaging process of the magnetic resonance device, detecting a RF signal of the magnetic resonance device, recording a trigger time of the RF signal, generating an enable signal triggering the focused ultrasound device to start heating based on the trigger time of the RF signal, and controlling a heating duration of the focused ultrasound device according to echo time TE. That is, after enabling the trigger signal, the focused ultrasound device starts to work, and by the control of time sequence, the treatment proceeds for a period of time and stops to work before echo signals collection.

Some specific embodiments of the present application are described in detail above. It should be understood that those skilled in the art can make many modifications and changes based on the concept of the present application without creative efforts. Therefore, any technical solutions that can be obtained by those skilled in the art by logical analysis, reasoning or limited experiments based on the concept of the present application and on the basis of the prior art should be within the scope determined by the claims.

What is claimed is:

1. A compatible system for synchronized working of magnetic resonance imaging and focused ultrasound thermal ablation, comprising a magnetic resonance device and a focused ultrasound device, wherein the system further comprises a signal collector and a control circuit connected to the signal collector; and in an imaging process of the magnetic resonance device, the signal collector is configured to detect a radio frequency (RF) signal of the magnetic resonance device, and the control circuit is configured for recording a trigger time of the RF signal, generating an enable signal triggering the focused ultrasound device to start heating based on the trigger time of the RF signal, and controlling a heating duration of the focused ultrasound device according to an echo time;

wherein the generating the enable signal triggering the focused ultrasound device to start working based on the trigger time of the RF signal comprises:

calculating an error value between a trigger time difference and a time of repetition (TR) cycle according to the trigger time difference between a current trigger time of the RF signal and an adjacent last trigger time of the RF signal, and determining whether the error value is less than a set threshold value;

in response to the error value being less than the set threshold value, generating the enable signal at the current trigger time of the RF signal; and in response to the error value being not less than the set threshold value, deleting the current trigger time of the RF signal.

2. The compatible system according to claim 1, wherein the set threshold value is less than 1 ms.

3. The compatible system according to claim 1, wherein the control circuit is configured for obtaining the trigger time of the RF signal by comparing voltage values of the RF signal, and recording the trigger time.

4. The compatible system according to claim 1, wherein the heating duration of the focused ultrasound device is controlled to be less than the echo time.

5. The compatible system according to claim 1, wherein the signal collector is an open-loop coil.

6. The compatible system according to claim 1, wherein a heating duration of the focused ultrasound device is less than or equal to a phase encoding number of imaging of the magnetic resonance device.

7. A compatible method for synchronized working of magnetic resonance imaging and focused ultrasound thermal ablation, wherein the method is configured for controlling a magnetic resonance device and a focused ultrasound device to work alternately and compatibly, and the method comprises:

in an imaging process of the magnetic resonance device, detecting a RF signal of the magnetic resonance device, recording a trigger time of the RF signal, generating an enable signal triggering the focused ultrasound device to start heating based on the trigger time of the RF signal, and controlling a heating duration of the focused ultrasound device according to an echo time;

wherein the generating the enable signal triggering the focused ultrasound device to start working based on the trigger time of the RF signal comprises:

calculating an error value between a trigger time difference and a time of repetition (TR) cycle according to the trigger time difference between a current trigger time of the RF signal and an adjacent last trigger time of the RF signal, and determining whether the error value is less than a set threshold value;

in response to the error value being less than the set threshold value, generating the enable signal at the current trigger time of the RF signal; and in response to the error value being not less than the set threshold value, deleting the current trigger time of the RF signal.

8. The compatible method according to claim 7, wherein the heating duration of the focused ultrasound device is controlled to be less than the echo time.

\* \* \* \* \*